United States Patent [19]

Brooks et al.

[11] Patent Number: 4,947,875

[45] Date of Patent: Aug. 14, 1990

[54] FLAVOR DELIVERY ARTICLES UTILIZING ELECTRICAL ENERGY

[75] Inventors: Johnny L. Brooks; Donald L. Roberts, both of Winston-Salem; Jerry S. Simmons, Rural Hall, all of N.C.

[73] Assignee: R. J. Reynolds Tobacco Company, Winston-Salem, N.C.

[21] Appl. No.: 242,083

[22] Filed: Sep. 8, 1988

[51] Int. Cl.$^5$ .......................... A24F 1/00; A24F 47/00
[52] U.S. Cl. .................................. 131/330; 131/273; 131/194; 131/195; 128/202.21; 128/203.27; 128/204.23; 128/204.24
[58] Field of Search ............... 131/330, 273, 194, 195; 128/202.21, 203.27, 204.23, 204.29

[56] References Cited

U.S. PATENT DOCUMENTS

| | | |
|---|---|---|
| 1,771,366 | 7/1930 | Wyss et al. . |
| 1,968,509 | 7/1934 | Tiffany . |
| 2,057,353 | 10/1936 | Whittemore, Jr. . |
| 2,104,266 | 1/1938 | McCormick . |
| 2,974,669 | 3/1961 | Ellis . |
| 3,200,819 | 8/1965 | Gilbert . |
| 3,889,690 | 6/1975 | Guarnieri . |
| 3,918,464 | 11/1975 | Kolodziej . |
| 4,133,318 | 1/1979 | Gross et al. . |
| 4,141,369 | 2/1979 | Burruss . |
| 4,164,230 | 8/1979 | Pearlman . |
| 4,193,411 | 3/1980 | Faris et al. . |
| 4,246,913 | 1/1981 | Ogden et al. . |
| 4,303,083 | 12/1981 | Burruss, Jr. . |
| 4,523,589 | 6/1985 | Krauser . |
| 4,564,748 | 1/1986 | Gupton . |
| 4,580,583 | 4/1986 | Green, Jr. . |
| 4,735,217 | 4/1988 | Gerth et al. . |
| 4,771,796 | 9/1988 | Myer . |

FOREIGN PATENT DOCUMENTS

| | | |
|---|---|---|
| 186280 | 7/1986 | European Pat. Off. . |
| 2653133 | 5/1978 | Fed. Rep. of Germany . |
| 2704218 | 8/1978 | Fed. Rep. of Germany . |
| 3300992 | 7/1984 | Fed. Rep. of Germany . |
| 2128256 | 10/1972 | France . |
| 48-8231 | 3/1973 | Japan . |
| WO86/02528 | 5/1986 | PCT Int'l Appl. . |
| 197946 | 4/1924 | United Kingdom . |

Primary Examiner—V. Millin

[57] ABSTRACT

Flavor delivery articles employ an electrical resistance heating element and an electrical power source to provide a flavored aerosol. The articles advantageously comprise a disposable portion and a reusable controller. The disposable portion normally includes a flavor substance and an air permeable resistance heating element having a surface area greater than 1 m$^2$/g, which usually carries an aerosol forming substance. The reusable controller normally includes a puff-actuated current actuation means, a time-based current regulating means to control the temperature of the heating element, and a battery power supply.

136 Claims, 8 Drawing Sheets

FLAVOR DELIVERY ARTICLES UTILIZING ELECTRICAL ENERGY

BACKGROUND OF THE INVENTION

The present invention relates to flavor delivery articles which employ an electrical resistance heating element and an electrical power source to produce a flavored aerosol.

Over the years, there have been proposed numerous smoking products, flavor generators and medicinal inhalers which utilize electrical energy to vaporize or heat a volatile material for delivery to the mouth of the user.

U.S. Pat. No. 2,057,353 to Whittemore, Jr. proposed a vaporizing unit. In particular, a wick reportedly carried liquid medicament by capillary action to a point where the liquid was vaporized by an electrical resistance heating element.

U.S Pat. No. 2,104,266 to McCormick proposed an article having a pipe bowl or cigarette holder which included a resistance coil (i) wound on an insulating and heat resisting material, and (ii) contained in an insulated chamber. Prior to use of the article, the pipe bowl was filled with tobacco or the holder was fit with a cigarette. Current then was passed through the resistance coil. Heat produced by the resistance coil was transmitted to the tobacco in the bowl or holder, resulting in the volatilization of various ingredients from the tobacco. A thermostatic switch was employed to maintain a predetermined temperature range to which the tobacco was heated.

U.S. Pat. No. 3,200,819 to Gilbert proposed a smokeless, non-tobacco cigarette having a flavor cartridge, such as a porous substrate impregnated with mentholated water. The article included a battery for powering a tube or bulb which was illuminated before assembly. The bulb was placed in a tubular liner, which was in turn located within a tube of plastic having the size, color and form of a cigarette. In use, the illuminated bulb reportedly heated the flavored air drawn through passages formed between the bulb and the tubular liner. As such, warm, moist, flavored air was delivered to the user.

French Patent Publication No. 2,128,256 to Ribot et al proposed an article for delivering denicotinized smoke. The proposed article included a sealed ampule which contained pressurized denicotinized smoke. An electric resistor was immersed in the smoke. In use, the terminals of the resistor were pushed into contact with a microbattery causing the resistor to generate heat and heat the smoke within the ampule. Draw by the user reportedly caused warm smoke to exit a valve near the mouthend of the article.

Japanese Patent Publication No. 8231/73 to Takeda proposed a cigar-shaped inhaler which included a battery powered Nichrome wire to heat air that, in turn, evaporated an essence from an essence container. The Nichrome wire was energized by either a manually-actuated or a draw actuated "on-off" switch.

West German Patent application No. 2,653,133 to Kovacs proposed a smoking simulator having an internal battery which could accelerate or control the vaporization or emission of aromatic substances for delivery to the user. In supplemental West German Patent application No. 2,704,218, Kovacs described the use of a vacuum or draw-actuated switch to switch "on" the battery operated heating coil.

A draw actuated, pressure transducer switch was described in U.S. Pat. No. 4,246,913 to Ogden et al, as part of a smoke aversion therapy article which delivered a small electrical shock to a smoker whenever the smoker drew on a cigarette.

U.S. Pat. No. 4,141,369 to Burruss proposed an article similar to the previously discussed McCormick articles. Burruss proposed a container which was electrically heated to a temperature sufficient to volatilize desired components from smoking material inserted therein. Heated air passing through the container during draw reportedly carried volatilized materials to the mouth of the user.

U.S. Pat. No. 4,303,083 to Burruss proposed a pipe having an electrical resistance heating element, a manually operated "on-off" power switch, and an opening above the resistance element for the addition of volatile compound. During use, the volatile compound was applied, using a squeeze tube or eye dropper, to a heated surface within the pipe, apparently on a puff-by-puff basis. The volatile compounds reportedly were vaporized, mixed with air drawn into the pipe, and inhaled by the user.

PCT Publication No. WO 86/02528 to Nilsson et al proposed an article similar to that described by McCormick. Nilsson et al proposed an article for releasing volatiles from a tobacco material which had been treated with an aqueous solution of sodium carbonate. The article resembled a cigarette holder and reportedly included a battery operated heating coil to heat an untipped cigarette inserted therein. A switch was activated to supply current to the heating coil. A temperature sensor reportedly disconnected and reconnected the battery in order to maintain the temperature generated by the device in a narrow temperature range. Air drawn through the device reportedly was subjected to elevated temperatures below the combustion temperature of tobacco and reportedly liberated tobacco flavors from the treated tobacco contained therein.

U.S. Pat. No. 4,735,217 to Gerth et al proposed a "cigarette-shaped" medicament dosing article having a pellet of vaporizable medicament and a Nichrome resistance heating element connected in series with a battery power source and a draw actuated switch. In their only working example, the Nichrome heating element allegedly achieved a temperature in the range of 190° F. to 220° F. (90° C. to 105° C.) within a two second puff, which apparently was sufficient to volatilize menthol from a menthol pellet. At Column 8, lines 43–63, Gerth et al. went on to speculate that their article could be used to vaporize nicotine from a nicotine-containing pellet and that they believed it feasible to coat the heating element with a nicotine-containing compound in lieu of using a vaporizable pellet.

However, it is believed that it would not be possible to coat a Nichrome heating element, of the type described by Gerth et al, with enough vaporizable liquid material to deliver sufficient volatile material to the user, over a 6 to 10 puff life. It also is believed that the article of Gerth et al would not be able to provide enough electrical energy to (i) vaporize volatile material until near the end of a typical two second puff, or (ii) provide a high enough temperature (e.g., 150° C. to 350° C.) to vaporize many volatile materials within a two second puff, including many desirable aerosol forming substances and many volatile flavor components. In addition, even with only a single AA battery, the article described by Gerth et al. is more than 3 times the diameter and many times heavier than a typical cigarette and is provided with a relatively imprecise draw actuated control switch and with no means of regulating the current or heat during the puff.

Despite many years of interest and effort, none of the foregoing articles employing electrical energy has ever realized any significant commercial success, and it is believed that none has ever been widely marketed. Moreover, it is believed that none of the foregoing electrical energy articles is capable of effectively providing acceptable flavor delivery to the user., especially a 6 to 10 puff, or greater, product life.

Thus, it would be desirable to provide a flavor delivery article which utilizes electrical energy and which is capable of delivering acceptable quantities of flavored aerosol over at least 6 to 10 puffs.

SUMMARY OF THE INVENTION

The present invention relates to flavor delivery articles which employ an electrical resistance heating element and an electrical power source to provide a flavored aerosol. Preferred articles can produce aerosol almost immediately upon commencement of a puff, as well as provide the controlled production of aerosol throughout the puff and over a 6 to 10 puff product life.

In one aspect of the invention, the flavor delivery article includes a disposable portion (e.g., a cartridge) which utilizes an air permeable high surface area electrical resistance heating element that normally carries aerosol forming and/or flavor substances prior to use. This resistance heating element typically is a porous material having a surface area greater than 1 $m^2/g$, as determined using the Brunaver, Emmett and Teller (BET) method described in *J. Am. Chem. Soc.*, Vol. 60, p. 309 (1938); and *Adsorption Surface Area and Porosity*, Gregg et al, Academic Press, NY (1967). Preferably, the heating element is a fibrous carbon material, most preferably having a surface area greater than about 1,000 $m^2/g$. (In contrast, the surface area of the Nichrome metal resistance element of Gerth et al is believed to be about 0.01 $m^2/g$.) Preferably, such porous heating elements are impregnated with liquid aerosol forming substances, such as glycerin, and with a flavor such as a coffee extract or menthol. Such heating elements are particularly advantageous in that they are capable of holding and efficiently releasing relatively large quantities of liquid aerosol forming substances and flavor materials. For example, such heating elements can carry enough aerosol forming substances to provide aerosol for 6 to 10 puffs, or more.

Another important aspect of the invention relates to the various configurations of the disposable portions described herein. For example, in certain preferred embodiments, the disposable portion advantageously is provided with an electrical connection means at one end thereof. This electrical connection means includes means for connecting the resistance element to a battery or other external power source, and preferably includes an air passageway used in conjunction with the preferred puff actuated current actuation means. In other preferred embodiments, the disposable portion is adapted for connection to the external power source via connectors located on the reusable controller. In certain preferred embodiments, the resistance heating element is located centrally in the disposable portion and/or does not occupy a significant portion of the cross-sectional area of the disposable portion. In other preferred embodiments, the resistance heating element is located adjacent an end of the disposable portion, and/or at least substantially fills the cross-sectional area of the disposable portion or the air passageway therethrough.

A reusable controller can be used with the disposable portions of the invention. This reusable controller normally includes a current actuation means, a separate current regulating means to control the temperature of the heating element, and a battery power supply. Alternatively, the electrical power supply can be provided separately from the current actuation and current regulating means; e.g., as a separate battery pack or as normal household current stepped down by an appropriate transformer. The reusable controller can be in the form of a pipe, a reusable mouthpiece, a hand-held unit or other portable form into which the disposable portion can be inserted. The use of such a reusable article with the disposable portions of the invention is particularly advantageous in that it permits the use of (i) relatively large power sources, capable of generating 10 to 40 watts of power or more, and (ii) accurate and sophisticated current actuation and current regulating means that normally would be too costly to incorporate into a single use, disposable article.

Preferably, the current actuation means is puff actuated, so that current flows through the resistance heating element to produce flavored aerosol only during draw by the user.

To use the articles of the invention, the user simply inserts the disposable portion containing the flavor substance into the controller, to electrically connect the heating element to a circuit including the current actuation and current regulating means and to the battery. When the user draws on the mouthend of the article, the preferred current actuation and current regulating means permit unrestricted or uninterrupted flow current through the resistance heating element to generate heat rapidly. This heating volatilizes the aerosol forming substances and/or flavors, which in turn form an aerosol and pass through the article and into the mouth of the user. At the same time, the current regulating means (i) regulates current flow through the heating element to control heating of the resistance element and the temperature experienced thereby, and (ii) prevents overheating and degradation of the aerosol former. When the user stops drawing on the article, the current actuation means prevents further current flow through the heating element and disables the current regulating means. This process continues, puff after puff, until the user decides to stop drawing on the article. At that point, the disposable portion can be removed and discarded, and a new one inserted in its place.

In another aspect of the invention, the current actuation means, the current regulating means, and/or the electrical power source may be incorporated into the portion of the article containing the electrical resistance heating element, so that the reusable controller may be reduced in size or even eliminated.

Preferred flavor delivery articles of the invention are capable of delivering an average of at least 0.5 mg, more preferably at least 0.8 mg, of aerosol and/or flavor substance per puff, measured as wet total particulate matter (WTPM), under conditions of 2 second, 35 ml puffs, taken once every 60 seconds. Preferred articles of the invention can deliver such material, preferably in visible form, for a plurality of puffs, preferably at least about 6 puffs, more preferably at least about 10 puffs, under such conditions.

As used herein, and only for the purposes of this application, "aerosol" is defined to include vapors, gases, particles, and the like, both visible and invisible, generated by action of heat from the resistance heating element upon aerosol forming substances and/or flavor substances located on the resistance element or elsewhere in the article.

The articles of the present invention are described in greater detail in the accompanying drawings and in the detailed description of the invention which follows.

DETAILED DESCRIPTION OF THE PREFERRED EMBODIMENTS

Figures 1, 1A:
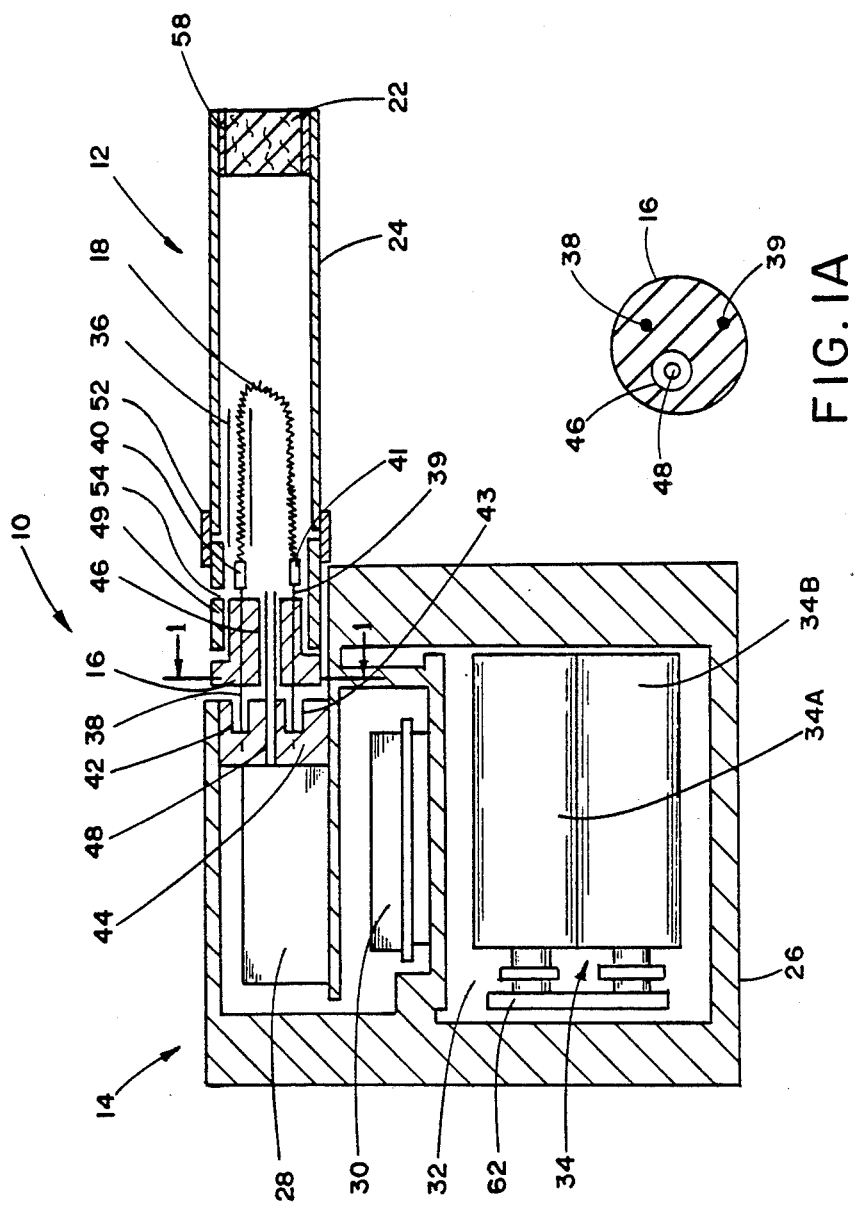
FIG. 1 is a longitudinal, partial sectional view of an article of this invention.
FIG. 1A is a sectional view of a portion of the embodiment shown in FIG. 1 taken along lines 1—1.

Referring to FIG. 1, flavor delivery article 10 includes a disposable cartridge 12 and a reusable, handheld controller 14. The disposable cartridge 12 includes electrical connection plug 16, resistance heating element 18 carrying an aerosol forming substance, mouth end filter 22, and a resilient overwrap 24. The preferred controller 14 includes a case 26, a puff actuated current actuation mechanism 28 having the form of a pressure sensitive switch, a time-based current control circuit 30, and a chamber 32 into which battery power supply 34 (shown as batteries 34A and 34B) is inserted.

The resistance heating element 18 employed in cartridge 12 preferably is a fibrous material having a high surface area and an adsorbant, porous, wettable character, in order to carry a suitable amount of aerosol forming substance for effective aerosol formation. Suitable heating elements preferably have surface areas above about 50 m$^2$/g, more preferably above about 250 m$^2$/g, and most preferably above about 1,000 m$^2$/g.

Preferred heating elements normally have low mass, low density, and moderate resistivity, and are thermally stable at the temperatures experienced during use. Such heating elements heat and cool rapidly, and thus provide for the efficient use of energy. Rapid heating of the element also provides almost immediate volatilization of the aerosol forming substance. Rapid cooling prevents substantial volatilization (and hence waste) of the aerosol forming substance during periods when aerosol formation is not desired. Such heating elements also permit relatively precise control of the temperature range experienced by the aerosol forming substance, especially when the preferred time based current control means described herein is employed.

Preferred resistance heating elements include carbon filament yarns available from American Kynol, Inc., New York, NY, as Catalog Nos. CFY-0204-1, CFY-0204-2, and CFY-0204-3. Such yarns reportedly have surface areas of about 1,500 m$^2$/g and resistivities of about 10 to about 30 milliohm-cm. See, Kirk-Othmer: *Encyl. Chem. Tech.*, Vol. 16, 3rd Ed., pp 135–136 (1981). Representative lengths of such yarns range from about 15 to about 50 mm. Other preferred heating elements include carbon felts and activated carbon felts available from American Kynol, Inc., as Catalog Nos. CN-157(HC), CN-210(HC), ACN-211-10, ACN-210-10, and ACN-157-10. Such felts typically have surface areas of about 1,500 m$^2$/g and resistivities of about 5 to about 30 milliohm-cm. Such felts can be used in the form of circular discs having diameters of about 4 to 8 mm, as described in greater detail hereinafter with reference to FIGS. 4-6. Other suitable heating elements include porous metal wires or films; carbon yarns, cloths, fibers, discs or strips; graphite cylinders, fabrics or paints; microporous high temperature polymers having moderate resistivities; porous substrates in intimate contact with resistance heating components; and the like.

Preferably, the heating element 18 is impregnated with or otherwise carries one or more aerosol forming substances in order that the aerosol forming substances are in a heat exchange relationship with the electrical heating element. The aerosol forming substances used in this invention are capable of forming aerosol during periods when the heating element generates heat. Such substances preferably are composed of carbon, hydrogen and oxygen, although other material such as water can be employed. The aerosol forming substances can have a solid, semi-solid, or liquid form. Examples of suitable aerosol forming substances include water; ethanol; polyhydric alcohols such as glycerin, propylene glycol and triethylene glycol; aliphatic esters of mono-,di-, or poly-carboxylic acids such as methyl stearate, dimethyl dodecandioate, dimethyl tetradecandioate; a flavor such as menthol, chocolate, coffee, fruit or artificial fruit; and the like, as well as mixtures thereof.

While the loading of the aerosol forming substance can vary from substance to substance and from heating element to heating element, the amount of liquid aerosol forming substance used typically will be greater than about 15 mg and preferably ranges from about 25 mg to about 50 mg.

The flavor substances used in this invention are those which are capable of being delivered to the user in aerosol form. Such flavors include menthol, peppermint, spearmint, cinnamon, vanilla, licorice, ginger, mouth fresheners, chocolate, coffee and coffee flavors, liqueurs, root beer, spice, nut, pepper, pizza, bacon, sausage, cereal, popcorn, cookie, strawberry, citrus, raspberry, cherry, tooty fruity, and the like.

Such flavor substances can be used as aerosol forming substances, and can be carried by the resistance heating element. Such flavor substances also can be placed between the resistance heating element and the mouthend of the cartridge, such as in mouthend filter 22 or in a separate flavor chamber or cartridge located between the resistance heating element and the filter. In such instances, the flavor substance can either form an aerosol or be eluted by the aerosol forming material. As with the aerosol forming substance, the loading of the flavor substance can vary from substance to substance, and depends upon the taste desired.

A heat resistant, electrically insulative strip, tube or spacer 36, preferably is provided in order to maintain the heating element in place and to prevent the heating element from contacting itself. The insulative spacer 36 can be a cellulosic sheet treated with fire retardant, an aluminum foil having a surface coating of aluminum oxide, an insulative ceramic material, a heat resistant plastic material such as a polyimide, or the like.

The electrical connection plug 16 preferably is manufactured from a resilient, electrically insulative material such as a thermoplastic material. The plug 16 includes two electrical connector pins or prongs 38, 39 connected to the ends of heating element 18 via connectors 40, 41. The pins 38, 39 engage with electrical terminals 42, 43 located in electrical connection receptacle 44 of the controller 14. Plug 16 also includes a passageway 46 through which tube 48 from pressure sensing switch 28 extends. As shown in FIG. 1A pins 38, 39 and passageway 46 are offset with respect to the longitudinal axis of plug 16.

A portion of the length of the electrical connection plug 16 preferably is circumscribed by a collar 49 having the form of a thermoplastic tube, which preferably is friction fit around a portion of the length of the plug. The collar 49 in turn is secured to the remaining portion of the cartridge via overwrap 24 using tipping paper 52 or other appropriate means such as adhesive, a friction fit, or the like. Preferably, the collar 49 includes one or more peripheral air inlet openings 54 which provide a flow of ambient air through the cartridge during draw. Alternatively, the air inlet can be positioned through the extreme inlet end of the cartridge or elsewhere through the periphery of the cartridge, such that drawn ambient air passing through the cartridge to the mouth of the user passes the resistance element.

The mouthend filter 22 is provided for aesthetic purposes. It preferably is a low efficiency filter made from a melt blown thermoplastic such as polypropylene. For example, the filter can be manufactured by pleating a web of nonwoven polypropylene available from Kimberly-Clark Corp. as experimental melt blown, macrofiber polypropylene PP-100-F. Alternatively, the mouthend filter 22 can be manufactured from cellulose acetate tow, or the like. Preferably, the filter material is overwrapped with a paper plug wrap 58.

To maximize aerosol and flavor delivery which otherwise would be diluted by radial (i.e., outside) air infiltration through the overwrap 24, one or more layers of non-porous paper can be used to envelop the cigarette. Examples of suitable non-porous papers are cigarette papers commercially available from Kimberly-Clark Corp. as KC-63-5, P878-5, P878-16-2 and 780-63-5. If desired, the overwrap can be a resilient paperboard material, foil-lined paperboard, or the like; and the paperboard can be circumscribed by a cigarette paper wrap.

The reusable controller 14 includes a case 26 or outer housing which provides a convenient and aesthetic holder for the user. The outer housing 26 can have a variety of shapes and can be manufactured from plastic, metal, or the like. Controller 14 includes an insulative receptacle 44 which includes plug-in connectors 42, 43 for engagement with prongs 38, 39 of plug 16. Receptacle 44 also includes tube 48 which is inserted into passageway 46 of plug 16 to be in airflow communication with the internal region of the cartridge. The other end of tube 48 is in airflow communication with pressure sensing switch 28, so that changes in air pressure which occur within the cartridge during draw can be sensed by the switch.

Controller 14 also preferably includes a control circuit 30, which is connected to a puff actuated, differential pressure sensitive switch 28 by electrically conductive wires (not shown), as well as to batteries 34A and 34B via battery terminal 62. The control circuit 30 preferably is time based. That is, the preferred current control circuit preferably is based on controlling the time period during draw during which current passes through the resistance element. This time based control, in turn, controls the temperature experienced by the resistance element and by the aerosol forming substances. Preferred pressure sensitive switches and control circuits, and their connection power source 34 and resistance element 18, are described in greater detail hereinafter with reference to FIGS. 9 and 10.

While the heat needed to volatilize the aerosol forming substance (and the flavor forming substance in appropriate cases) during a puff varies for each particular substance, sufficient heat usually is necessary, during a puff, to heat the aerosol forming substance to a temperature above about 120° C. in order to volatilize an appropriate amount of the aerosol forming substance. More typically, a temperature above about 150° C., often above about 200° C., and sometimes as high as about 300° C. to about 350° C., is necessary to volatilize adequate amounts of the aerosol forming substance during a puff. However, it is desirable to avoid heating the aerosol forming substance to temperatures substantially in excess of about 550° C. in order to avoid degradation and/or excessive, premature volatilization of the aerosol forming substance.

For a particular resistance heating element and a particular aerosol forming substance, a sufficient current is required, during each puff, to generate the heat necessary to volatilize enough aerosol forming substance to provide an adequate amount of delivered aerosol. For the preferred aerosol forming substances and the preferred carbon heating elements described herein, an 18 volt battery usually generates sufficient power (i.e., about 18 watts) to heat the aerosol forming substance to a suitable temperature to volatilize the aerosol forming material almost immediately after current actuation, i.e., within about 0.5 second, preferably within about 0.1 second. The 18 volt battery can be provided using two fully charged 9 volt manganese dioxide-zinc transistor batteries (as shown in FIG. 1) or three 6 volt lead acid batteries. Also useful is a silver-zinc alkaline battery using potassium hydroxide as an electrolyte and having about 12 to about 15 single cells connected in series, wherein the surface area of each positive electrode is about 3.25 $cm^2$. Other batteries can include nickel-zinc or nickel-cadmium batteries.

In use, the user inserts the plug 16 of the cartridge 12 into the receptacle 44 of the controller 14. Such action provides electrical connection of the resistance heating element 18 with the switch 28, the control circuit 30 and the batteries 34A and 34B. Such action also provides for airflow communication between the switch 28 and the inner portion of the cartridge. When the user puffs on the mouthend of the cartridge, ambient air enters the cartridge through air inlet 54. The pressure actuated switch 28 responds to a sensed change in air pressure within the cartridge during draw and permits current flow through the heating element 18. As a result, the heating element experiences an increase in temperature which in turn heats and volatilizes the aerosol forming substance. The volatilized aerosol forming substance mixes with the drawn air and forms an aerosol. The volatilized aerosol forming substance (in aerosol or vapor form) exits the mouthend filter 22 into the mouth of the user. During the puff, the preferred current control circuit (described in detail hereinafter) regulates the flow of current to control the temperature experienced by the heating element and the amount of aerosol forming substance which is volatilized.

If the flavor substance is carried by the resistance heating element, it normally volatilizes and passes to the mouth of the user in a manner similar to the aerosol forming substance. If not carried by the resistance heating element, the flavor substance is either volatilized by heat generated by the resistance heating element or eluted by the aerosol forming material as the aerosol forming material passes through the article.

When the user stops drawing on the cartridge, the pressure actuated switch 28 again responds to the sensed change in air pressure within the cartridge, and further current flow through the heating element ceases. As a result, the temperature of the heating element and the aerosol former quickly drop below the volatilization temperature of the aerosol former, and aerosol formation ceases. This process continues, puff after puff, normally for at least about 6 puffs, until aerosol delivery drops below the level desired by the user. Then, the user can remove the cartridge 12 from the control pack 14, and dispose of the cartridge. The user then can select a new cartridge, insert the new cartridge into the reusable controller, and repeat the flavor delivery process.

Figure 2:
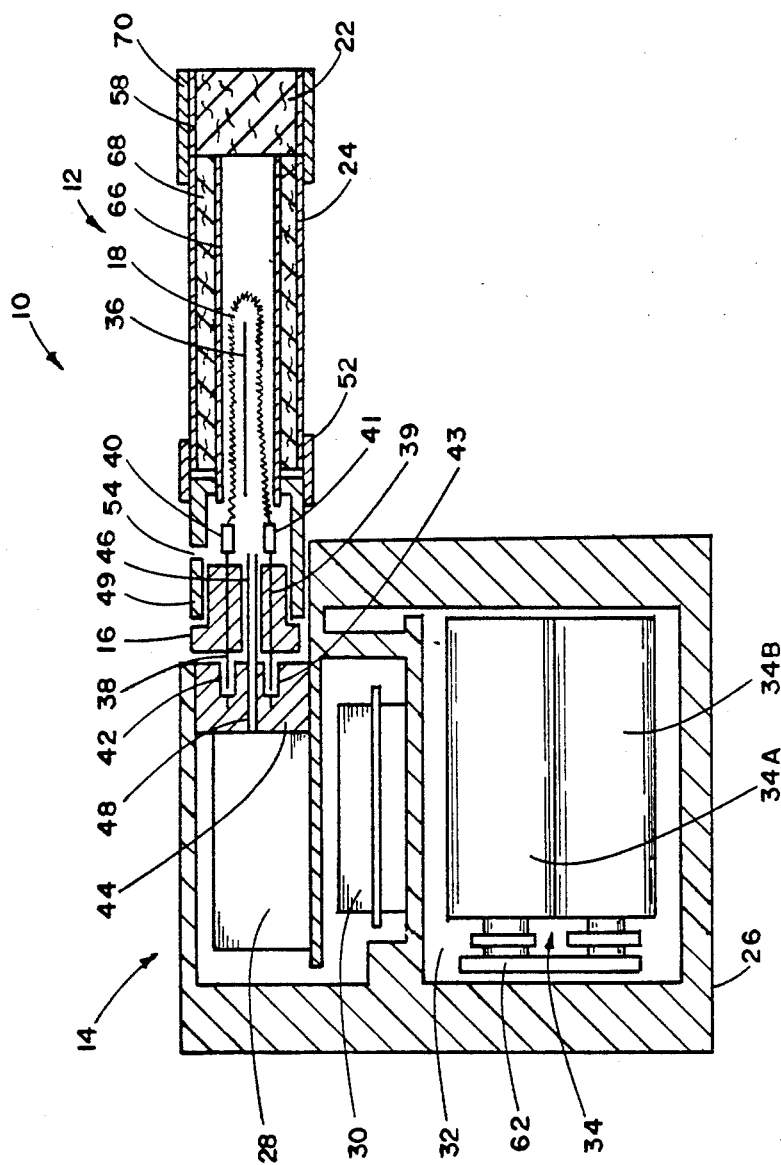
FIG. 2 is a longitudinal, partial sectional view of an article of this invention.

The embodiment illustrated in FIG. 2 is generally similar to the embodiment of FIG. 1, except that the heating element 18 is positioned within a heat resistant, insulative tube 66. The insulative tube 66 preferably is manufactured from a ceramic, a heat resistant cellulosic, an aluminum tube having a surface coating of aluminum oxide, a high temperature plastic such as a polyimide, or the like. Preferably, a plasticized cellulose acetate tube 68 circumscribes the insulative tube 66, and is itself circumscribed by paper overwrap 24. This embodiment also includes tipping overwrap 70 circumscribing the mouthend of the cartridge in order to attach filter element 22 to the remaining portion of the cartridge.

Figure 3:
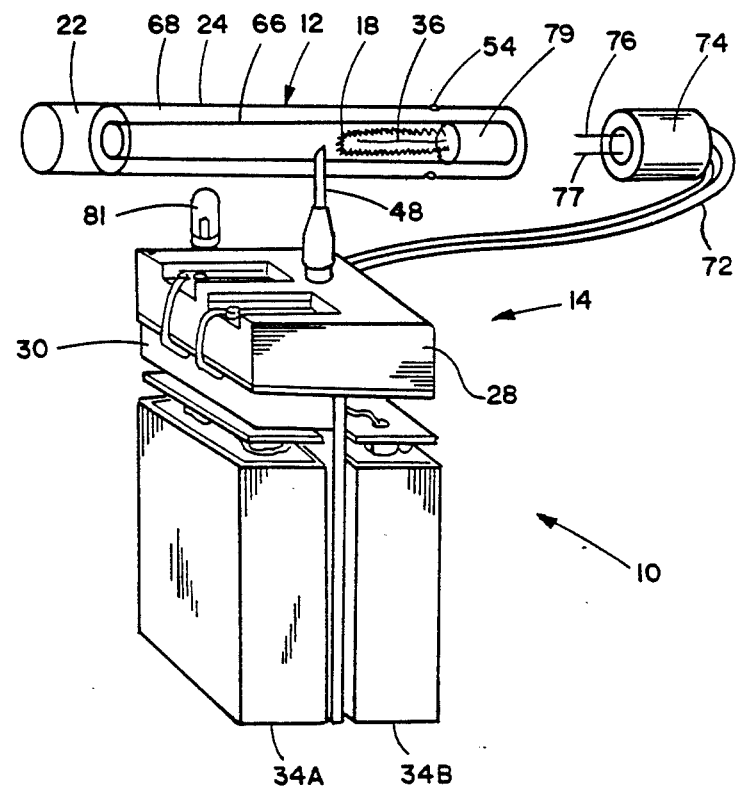
FIG. 3 is a perspective of an article of this invention including an exposed inner view of the reusable portion thereof.

Referring to FIG. 3, the illustrated embodiment is generally similar to the embodiment of FIG. 2, except that the controller or power pack 14 includes a flexible, cord-like connector 72 which terminates in a plug 74 having prongs 76, 77 for electrical connection into a receptacle 79 at one end of cartridge 12. A needle-like tube 48 extends from switch 28 and extends through resilient overwrap 24 in order that changes in air pressure within the cartridge during draw can be sensed by the switch. If desired, the tube 48 can be incorporated into the cord-like, connector 72 and extend into the cartridge through the receptacle 79. With such a design, it is possible for the user to place the control pack in a shirt pocket or on a table, and hold the cartridge in a normal fashion, without holding the added weight of the control pack in his/her hands. A light emitting diode 81 is positioned near the differential switch 28. The diode 81 is electrically connected to the electrical circuitry (as described hereinafter) such that it emits light during draw. As such, the user has a visual means for identifying periods when current passes through the resistance heating element 18.

Figure 4:
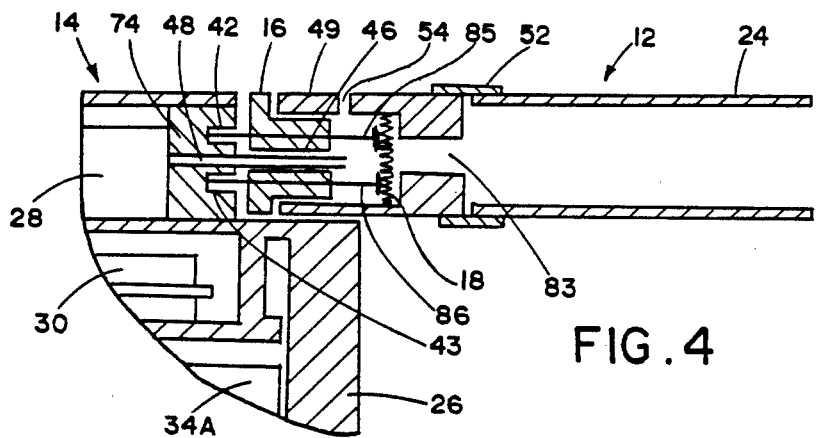
FIGS. 4, 5, and 6 are longitudinal, partial sectional views of preferred articles of this invention showing the disposable portions and cut-away views of the controllers.

Referring to FIG. 4, the illustrated embodiment is generally similar to the embodiment of FIG. 1, except that the heating element 18 is a circular disc or pad, preferably formed from an American Kynol carbon felt. The pad is permeable to airflow, and is disposed across an air passageway 83 in tubular collar 49 so that drawn air entering the cartridge 12 through opening 54 passes through the heating element 18. Electrical connection pins 85, 86 from plug 74 contact the heating element and help hold it in place against collar 49. In this embodiment, the collar 49 can be a thermoplastic material, a thermally stable plastic material, a ceramic, or the like.

Figure 5:
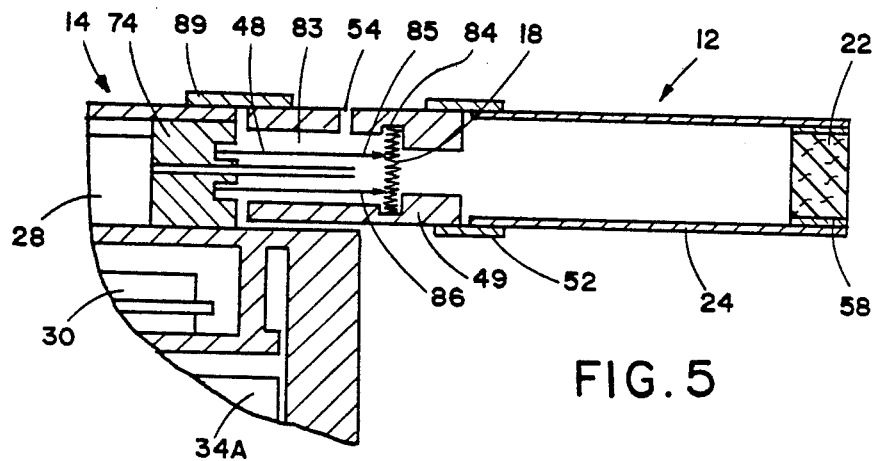

The embodiment illustrated in FIG. 5 is generally similar to the embodiment of FIG. 1. In this embodiment, the heating element 18 is a circular disc or pad of carbon felt disposed across an air passageway 83 extending through tubular collar 49. The pad is held in place by shoulder 84 on the collar 49. In addition, the cartridge does not have an electrical connect plug. Instead, electrical connection pins 85, 86 for the heating element extend from a plug 74 located on the controller 14. The cartridge 12 is held in place relative to the controller 14 via a clip 89 extending from the controller, or other suitable connection means.

Figure 6:
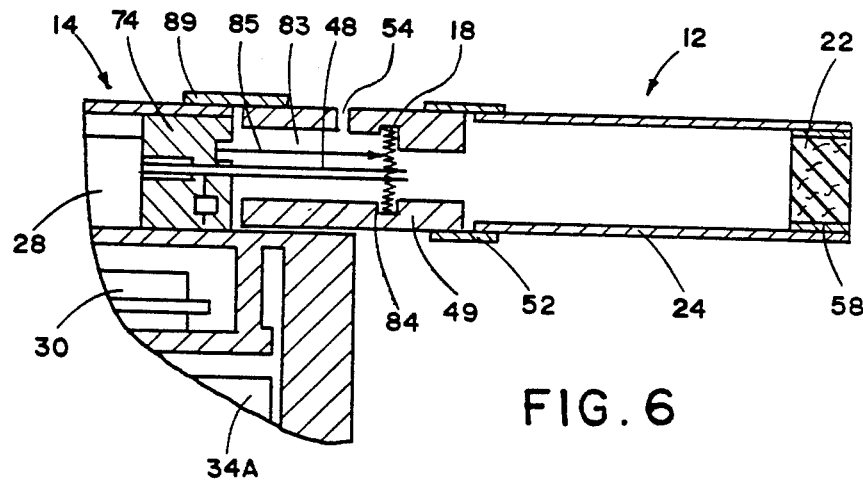

The embodiment illustrated in FIG. 6 is generally similar to the embodiment of FIG. 5, except that the pressure sensing tube 48 also is used as one of the connecting pins (e.g., in lieu of connection pin 86 of FIG. 5).

Figure 7:
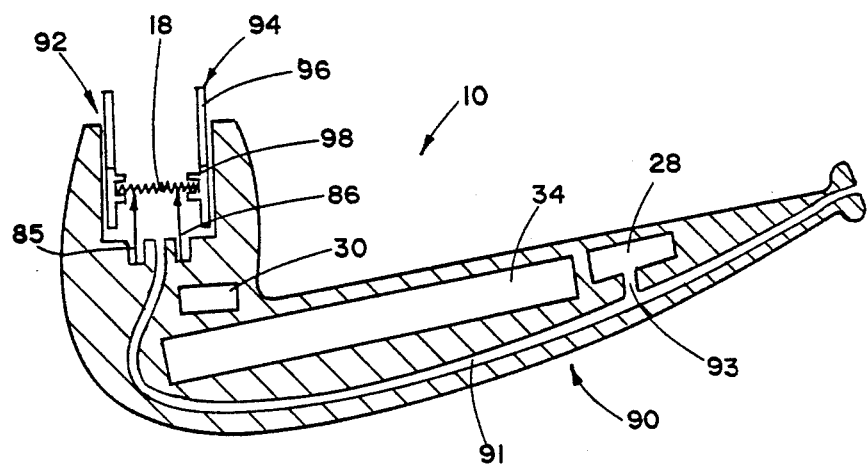
FIGS. 7 and 8 are longitudinal sectional views of additional articles of the invention.

Referring to FIG. 7, flavor delivery article 10 has the form of a pipe. The pipe includes a stem 90 having an air passageway 91 and a bowl 92 into which a disposable cartridge 94 is inserted. The bowl and stem can be manufactured from briarwood, or the like. The pipe 10 includes power source 34, such as one or more batteries, pressure sensing switch 28, pressure sensing passageway 93, current control circuit 30, and electrical pins 85, 86 extending from the bottom of the bowl. Preferred pressure sensing current control circuits and their connection to power source 34 and heating element 18 are described in greater detail hereinafter with reference to FIGS. 9 and 10.

The cartridge 94 includes an outer tubular housing 96 connected to a collar 98 which in turn supports resistance element 18 and the aerosol forming and flavor substances at one end of the cartridge. The resistance element 18 can be a carbon fiber felt pad which extends perpendicularly to the longitudinal axis of the cartridge so that drawn air passes through the resistance element. The disposable cartridge 94 is positioned within the bowl 90, with the resistance heating element 18 positioned near the bottom of the bowl so that the electrical connection pins 85, 86 extending from the bowl contact the resistance element.

Figure 8:
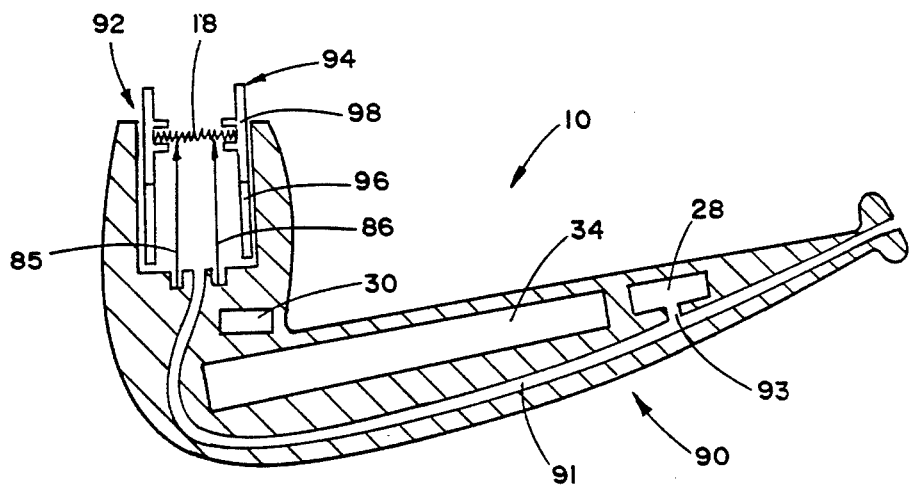

Referring to FIG. 8, the illustrated embodiment is generally similar to the embodiment of FIG. 7. In this embodiment, the resistance element 18 is positioned towards the air inlet end of the cartridge (i.e., remote from the bottom of the bowl) rather than near the air outlet end of the cartridge. In this case, the electrical connection pins 85, 86 extend from the bottom of the bowl to contact the resistance element 18.

Figure 9:
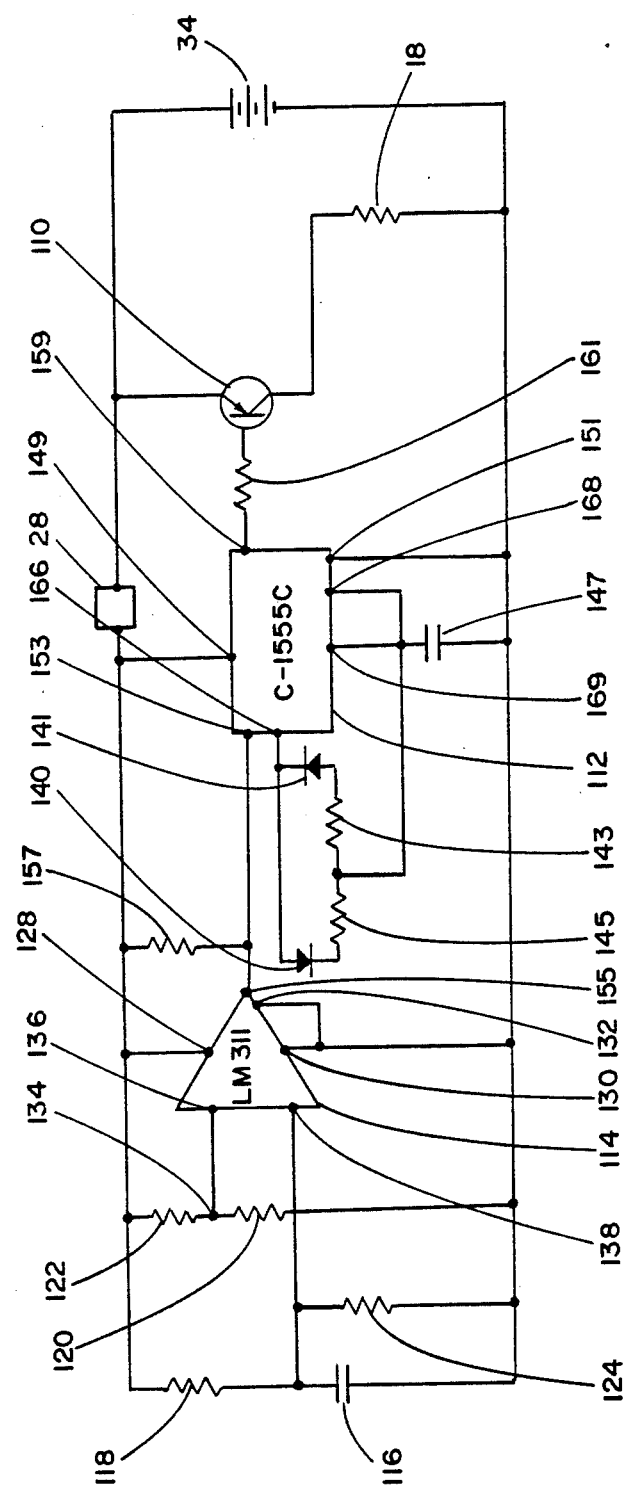
FIGS. 9 and 10 are representative schematic diagrams of time-based control circuits and related wiring for preferred controllers useful in this invention.

The foregoing embodiments preferably incorporate the preferred circuit shown schematically in FIG. 9. In particular, the circuit of FIG. 9 includes a power source 34, the electrical resistance heating element 18, a current actuation mechanism 28, and a preferred current regulating circuit or means for controlling the passage of current through the resistance element during periods of current actuation.

The circuit includes a puff actuated control switch 28, or some other suitable current actuation/deactuation mechanism, such as a manually actuated on-off switch, a temperature actuated on-off switch, or a lip pressure actuated switch. The preferred puff actuated switch 28 enables current to pass through the heating element 18 only during draw on the article. A typical puff actuated switch includes a means for sensing the difference in air pressure in a region within the previously described cigarette or disposable cartridge and an "on-off" switch responsive thereto.

A preferred puff actuated switch 28 is a pressure differential switch such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell Microswitch Microbridge Airflow Sensor, Part No. AWM 2100V from Microswitch Division of Honeywell, Inc., Freeport, Ill. Other suitable differential switches, analog pressure sensors, flow rate sensors, or the like, will be apparent to the skilled artisan.

The current regulating circuit preferably is time based. Normally, such a circuit includes a means for permitting uninterrupted current flow through the heating element for an initial time period during draw, and a timer means for subsequently regulating current flow until draw is completed. Preferably, the subsequent regulation involves the rapid on-off switching of current flow (e.g., on the order of about every 1 to 50 milliseconds) to maintain the heating element within the desired temperature range. Alternatively, the subsequent regulation involves the modulation of current through the heating element to maintain the heating element within a desired temperature range.

One preferred time-based current regulating circuit preferably includes a transistor 110, a timer 112, a comparator 114, and a capacitor 116. Suitable transistors, timers, comparators and capacitors are commercially available and will be apparent to the skilled artisan. Exemplary timers are those available from NEC Electronics as C-1555C and from General Electric Intersil, Inc. as ICM7555, as well as various other sizes and configurations of so-called "555 Timers". An exemplary comparator is available from National Semiconductor as LM311.

In the preferred circuit of FIG. 9, the means for determining the length of the initial time period of uninterrupted current flow includes resistors 118, 120, 122 and 124; capacitor 116; and comparator 114. The comparator 114 is powered by connection to entrance pin 128 and to ground pins 130, 132. Resistors 122 and 120 constitute a voltage divider which provides a predetermined reference or threshold voltage at the voltage divider tap 134 (i.e., the common point between resistors 122 and 120). The voltage divider tap 134 is connected to the negative entrance pin 136 of comparator 114. Capacitor 116 is connected in parallel with resistor 124. The parallel combination of capacitor 116 and resistor 124 is connected in series with resistor 118 at one end and to the ground reference point of the power source 34 at the other end. The other end of resistor 118 is connected to power source 34 via switch 28. The common node point between the resistor 118 and the parallel combination of capacitor 116 and resistor 124 is connected to the positive entrance pin 138 of comparator 114.

Resistors 118 and 124 and the capacitance of capacitor 116 are chosen so that the charge rate of capacitor 116 approximates the heating and cooling rate of the resistance heating element 18. The ratio of the resistance of resistor 124 to the sum of the resistances of resistors 118 and 124 sets the maximum voltage to which capacitor 116 can charge. Preferably, the resistances of voltage divider resistors 120 and 122 provide a voltage which is slightly below the maximum capacitor voltage set by resistors 118 and 124.

The timer means for regulating (or interrupting) current flow after the initial time period includes timer 112, diodes 140, 141, resistors 143, 145, and capacitor 147. This timer means generates a periodic digital wave having a preset on-off duty cycle, which is used to rapidly switch the current "on" and "off" at transistor 110 after the passage of the initial time period, to control the temperature range experienced by the resistance heating element.

Timer 112 is powered by connection through entrance pin 149 and ground pin 151. The reset pin 153 of timer 112 is connected to output pin 155 of comparator 114. As a result, the comparator 114 disables the timer during the initial period of uninterrupted current flow. A resistor 157 provides a so-called "pull-up" function for the reset pin 153 of timer 112.

Timer 112 also is connected to diodes 140, 141 at discharge pin 166. Diodes 140, 141 are in turn connected to resistors 145 and 143, respectively. In addition, timer 112 is connected to resistors 143 and 145, and capacitor 147 through trigger pin 168 and threshold pin 169. Capacitor 147 is provided to set the overall time period of the duty cycle. Preferably capacitor 147 is one which charges and discharges at a rapid rate in order that a relatively rapid duty cycle (e.g., in the order of 1 to 50 milliseconds) is provided.

Resistor 145 determines the charge rate of capacitor 147, and thus the "off" period of the duty cycle, while resistor 143 determines the discharge rate of the capacitor and thus the "on" period of the duty cycle. Diode 140 acts to allow current flow from the timer 112 through resistor 145 and to capacitor 147 during periods when the capacitor is charging, and prevents current passage through resistor 145 when the capacitor is discharging. Diode 141 acts to allow current flow from the capacitor 147 through resistor 143 and to the timer during periods when the capacitor is discharging, and prevents current passage through resistor 143 when the capacitor is charging. Thus, the relative on-off duty cycle of the wave form can be varied by selection of the resistances of resistors 143 and 145.

The output pin 159 of timer 112 is connected to resistor 161. The resistor 161 is in turn connected to the base of transistor 110 in order to limit "on" current through the base-emitter (BE) junction of the transistor. The transistor 110 acts to control the relatively large current which passes through the resistance element 18 from the power source 34 by switching "on" and "off" in response to current flow from the timer.

When draw commences, the puff actuated switch 28 closes to allow current flow through the circuit. The normally "off" transistor switches "on" in response to current flow through the timer 112. This allows current to flow through the resistance heating element 18.

Simultaneously, capacitor 116 begins to charge. When capacitor 116 is charged to the predetermined threshold voltage determined by resistors 120 and 122, which typically occurs in about 1 second, comparator 114 activates timer 112 through reset pin 153. This terminates the uninterrupted current flow to the transistor 110 by switching the transistor "off." At the same time, the timing means begins generating the periodic digital wave form having a preset on-off duty cycle at output pin 159. Such action of the timing means in turn causes the transistor to switch "on" and "off" rapidly, thus rapidly enabling and disabling current flow through the heating element 18. This rapid switching acts to control the average current flow through the heating element, thus controlling the temperature range experienced by the heating element during the balance of a puff.

As described above, the capacitance of capacitor 147 determines the overall time period of the preset duty cycle, while the relative "on" and "off" periods of the duty cycle are determined by the relative resistances of resistors 143 and 145. By varying these resistances, it is possible to closely control the temperature range experienced by the heating element 18, so as to provide a relatively steady state temperature range, or a controlled decrease or increase in the temperature range during the latter portion of a puff.

When draw ceases, puff actuated switch 28 opens to prevent further current flow through the circuit. As a result, the transistor 110 switches to its normally "off" position, thus preventing further current flow through the heating element 18. As a result, the heating element begins to cool, and volatilization of the aerosol forming and/or flavor substance ceases. At the same time, capacitor 116 begins to discharge, preferably at about the same rate at which the heating element cools.

When a subsequent draw commences, the puff actuated switch again closes, thus allowing current to flow through the circuit. If the subsequent draw is taken before the capacitor 116 has discharged completely (i.e., before the heating element has cooled completely), the capacitor 116 preferably recharges to the predetermined threshold voltage at about the same rate at which the heating element heats. This activates timer 112 and terminates the period of uninterrupted current flow at about the same time that the heating element 18 reaches the preferred temperature range. As such, the heating element is prevented from overheating during periods of rapid puffing by the user.

Figure 10:
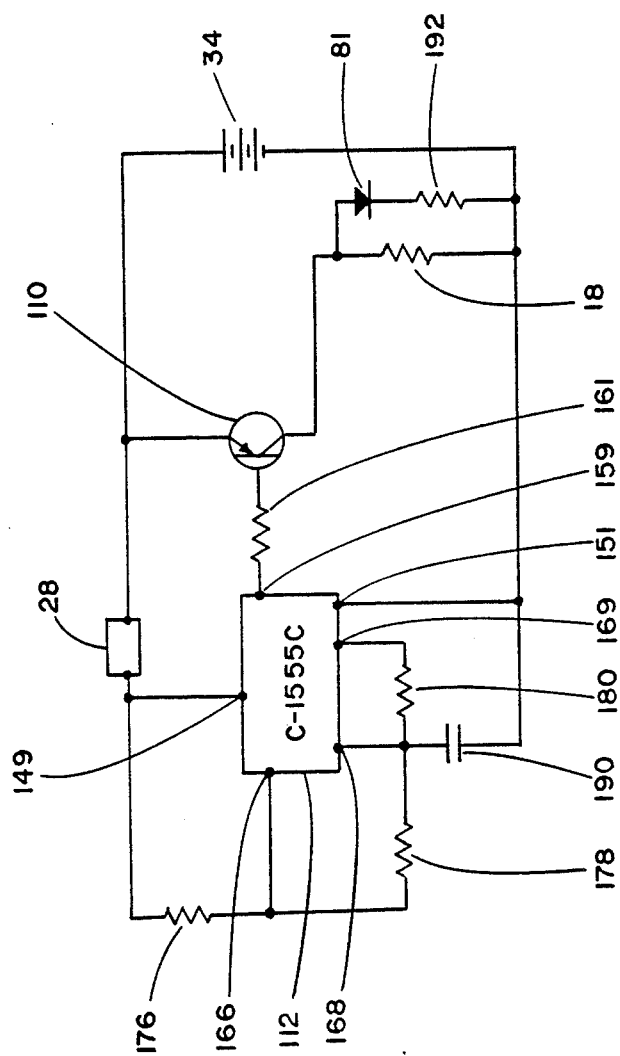

Controllers and flavor delivery articles of the invention also can incorporate the alternate time-based circuit shown schematically in FIG. 10. In particular, the circuit of FIG. 10 includes a power source 34, the electrical resistance heating element 18, a current actuation mechanism 28, and a current regulating circuit or means for controlling the passage of current through the resistance element during current actuation.

The preferred current actuation mechanism 28 is a puff actuated control switch of the type described previously.

The current regulating circuit shown in FIG. 10 is time based. This circuit includes timer 112, resistors 161, 176, 178 and 180, capacitor 190, and transistor 110.

Exemplary timers have been described previously. The timer 112 is powered by connection through entrance pin 149 and ground pin 151. The output pin 159 of the timer 112 is connected to the base of transistor 110 through resistor 161. The timer 112 is connected to resistor 180 through threshold pin 169; to the node point between resistors 180 and 178 through trigger pin 168; and to the node point between resistors 178 and 176 through discharge pin 166. The node point between resistors 180 and 178 is in turn connected to capacitor 190 which is connected to ground reference point of the power source 34.

The sum of the resistances of resistors 178 and 176 determines the period of uninterrupted current flow through resistance element 18, while the resistance of resistor 176 determines the period during which current flow is prevented from passing through the resistance element. Resistor 180 limits the voltage discharge rate of capacitor 190 so as to limit the initial heating time of the resistance element during a subsequent puff taken a short time after the preceeding puff.

If desired, light emitting diode 81 and resistor 192 can be employed. The light emitting diode 81 is connected in series with resistor 192. The series combination of diode 81 and resistor 192 is connected in parallel with the resistance element 18. The light emitting diode thus illuminates during draw, and the user then can have a visual means for identifying periods when current passes through the resistance element for heat generation. Such light emitting diodes also can be employed in the preferred circuit illustrated in FIG. 9.

When draw commences, the puff actuated switch 28 closes to allow current flow through the circuit of FIG. 10. The normally "off" transistor switches "on" in response to current flow through the timer 112, and in turn allows current to flow through the resistance heating element 18.

Simultaneously, capacitor 190 begins to charge. When capacitor 190 is charged to the predetermined voltage determined by resistors 178 and 176, timer 112 acts to switch the transistor 110 and current flow through heating element 18 "off." However, after a further period of time determined by resistor 176, the timer 112 again is turned "on." This process repeats itself until draw ceases. As such, the temperature experienced by the resistance element can be controlled so as to not overheat during a relatively long draw period. For example, a duty cycle can consist of an "on" period of uninterrupted current flow immediately upon draw for about 1.5 to about 2 seconds, followed by an "off" period of about 0.5 to about 1 second.

When draw ceases, puff actuated switch 28 opens to prevent further current flow through the circuit. As a result, the transistor 110 returns to its normally "off" position, thus preventing further current flow through the resistance element 18. The resistance element cools, and volatilization of the aerosol forming and/or flavor substance ceases. At the same time, capacitor 190 discharges.

Current regulating means which modulate current flow through the heating element can be employed in place of the previously described on-off time-based circuits. In addition, on-off and current modulating means can be connected to temperature sensors or other sensing means, rather than to a time-based circuit, in order to control the passage of current through the resistance heating element. Such sensors can be temperature sensors such as infrared sensors, piezoelectric films or the like, or thermostats such as bimetallic strips. Such temperature sensors can sense either the temperature of the resistance element directly or the temperature of the air passing the heating element. Alternatively, the temperature sensors can sense the temperature of a second "model" resistance heating element having a heating and cooling character related to that of the aerosol carrying heating element. Another type of sensor which can be employed is a dynamic resistance sensor which senses the change in electrical resistance of the heating element during the heating period.

The following examples are provided in order to further illustrate the invention but should not be construed as limiting the scope thereof. Unless otherwise noted, all parts and percentages are by weight, and all sizes are approximate.

EXAMPLE 1

A flavor delivery article substantially as shown in FIG. 2 was prepared as follows:

A. Preparation of the Disposable Portion

End plug 16 was formed from a Delrin plastic cylinder to have a 2 mm long section of 8 mm diameter and a 3 mm long section of 7 mm diameter. The plug was provided with a passageway 46 of sufficient size to receive an 18 gauge needle 48 and two smaller passageways to receive electrical connector pins 38, 39.

The electric resistance heating element 18 was formed from a 32 mm length of carbon filament yarn obtained from American Kynol, Inc., under Catalogue No. CFY-0204-1. This heating element had a resistance of about 20 ohms and a reported surface area of about 1,500 $m^2/g$. The heating element was impregnated, dropwise, with 25 $\mu l$ of a liquid aerosol forming substance comprising a mixture of glycerin, propylene glycol and triethylene glycol, and 30 $\mu l$ of an artificial coffee flavor. The polyhydric alcohol mixture consisted primarily of glycerin.

Two 15 mm long crimp connectors 40, 41, including pins 38, 39, were obtained from Black Box Corp., Pittsburgh, Pa. under Catalog No. GH-FA810. Crimp connectors 40, 41 were attached to each end of the heating element 18. Pin 38 of the first connector 40 was inserted through one of the smaller passageways in the plug 16. The heating element then was folded over a 20 mm long, 5 mm wide strip of Kapton polyimide film 36, to keep the heating element from contacting itself, and pin 39 of the second connector 41 was then inserted through the second small passageway of the plug 16.

A 9 mm long Delrin tube 49 was fabricated from an 8 mm diameter cylinder. One section, 6 mm long, had a 7 mm inner diameter (I.D.), and a second section, 3 mm long, had a 4 mm I.D. A single air inlet hole 54 was made about 4 mm from the 4 mm I.D. end of the tube using a No. 64 drill bit. The 7 mm I.D. end of the tube 49 was then friction fit over the 7 mm end of plug 16.

A 39 mm long, 4 mm outer diameter Kapton polyimide tube 66 was slipped over the resistance element 18 and inserted about 4 mm into the 4 mm I.D. end of the Delrin tube 49. A 36 mm length of a 8 mm O.D. plasticized cellulose acetate tube 68, SCS-1 from American Filtrona Corp., was slipped over the polyimide tube. This tube 68 was then overwrapped with a layer of Kimberly-Clark P-850-192-2 paper 24.

A 10 mm long, low efficiency cellulose acetate filter 22 (8 denier per filament, 40,000 total denier) was fastened to the open end of the wrapped tubes with a layer of tipping paper 70. The overall length of the disposable portion 12 was about 55 mm.

B. Assembly of the Controller

A polystyrene housing for the controller was formed to provide chambers for a pressure sensitive switch, a current control circuit, and a battery power supply.

The pressure sensitive switch was the switch portion of a Model No. MPL-502-V, range A, differential switch obtained from Micro Pneumatic Logic, Inc. A 20 mm long 18 gauge steel needle 48 was inserted into the appropriate opening in the switch. A polymethylmethacrylate receptacle 44 having a length of 26 mm, a height of 12 mm and a width of 9 mm was formed with a hole for the gauge needle and fitted with two Black Box Model No. GH-FA820 plug-in connectors 42, 43. The receptacle was slipped over the needle and inserted into an appropriately sized opening in the case.

The control circuit employed is schematically illustrated in FIG. 9. It was designed to provide uninterrupted current flow through the heating element for 1 second after the commencement of a puff. During the balance of the puff, the control circuit was designed to alternately switch off for 5 milliseconds and then on for 5 milliseconds (a 50 percent duty cycle), until the pressure actuated control switch opened. Comparator 114 was a Model LM 311 obtained from National Semiconductor. As shown in FIG. 9, connections were made at entrance pin 128, ground pins 30 and 132, negative entrance pin 136, positive entrance pin 138, and output pin 155. Timer 112 was a Model C-1555C obtained from NEC Electronics. Connections to timer 112 were made at trigger pin 168, threshold pin 169, output pin 159, discharge pin 166, entrance pin 149 and ground pin 151. Transistor 110 was a Model MJE 2955 from Motorola Semiconductor Products. Diodes 140 and 141 were Type IN914 diodes from Fairchild Semiconductor Corp. Capacitor 116 had a capacitance of 2.2 $\mu F$. Capacitor 147 had a capacitance of 0.1 $\mu F$. The resistances of the resistors 118, 120, 122 and 124 were 1,000,000 ohm; 180,000 ohm; 1,000,000 ohm; and 820,000 ohm, respectively. The resistances of resistors 157, 143, 145 and 161 were 120,000 ohm; 39,000 ohm; 100,000 ohm; and 1,000 ohm, respectively.

The control circuit was connected to the switch, the receptacle for the plug on the disposable portion, and the battery terminals, as schematically illustrated in FIG. 9. The battery supply consisted of two 9 volt alkaline transistor batteries connected in series.

C. Use

The end plug 16 was placed against receptacle 44 to electrically connect the disposable portion to the controller and insert the needle into the disposable portion. The mouthend of the disposable portion was placed in the mouth of the user, and the article was drawn upon. The article produced visible aerosol and flavor on all puffs for 8 consecutive puffs.

EXAMPLE 2

An article similar to the article described in Example 1 was prepared, except that (i) the resistance element was a length of Kynol Catalogue No. CFY-0204-1 carbon fiber yarn having a resistance of 28.1 ohms, and (ii) the heating element was impregnated with 35.9 mg of glycerin.

The article was tested under conditions of 2 second, 35 ml puffs, taken every 30 seconds. The article produced visible aerosol on all puffs for a total of 10 puffs, and yielded 21.3 mg WTPM.

EXAMPLE 3

Kynol Catalogue No. CFY-0204-2 carbon fiber yarn having a length of about 32 mm had a resistance of 18 ohms was used to prepare a heat generating electrical resistance element. The yarn had 18 $\mu$l of glycerin applied thereto. Each end of the yarn was electrically connected to an 18 volt/1 ampere limited power source. The arrangement was equipped with the control circuit described in Example 1.

The assembly was actuated such that the resistance element generated heat for a 2 second interval once every 30 seconds. During each puff, the timing mechanism began to control current flow 1 second after current flow through the resistance element was commenced. The duty cycle provided by the timing mechanism was 10 milliseconds. Maximum current was allowed to flow through the resistance element over one half the duty cycle, and no current was allowed to flow through the resistance element over the other half of the duty cycle. As such, the average current experienced during the timer cycle period was about one half of the maximum current.

Voltage and current levels were measured over time, and the temperature of the resistance element was monitored over time using a Wahl Model HSM-672 IR Spy focused onto the resistance element. Values of the measured and monitored data were recorded, and are presented in FIG. 11.

Figure 11:
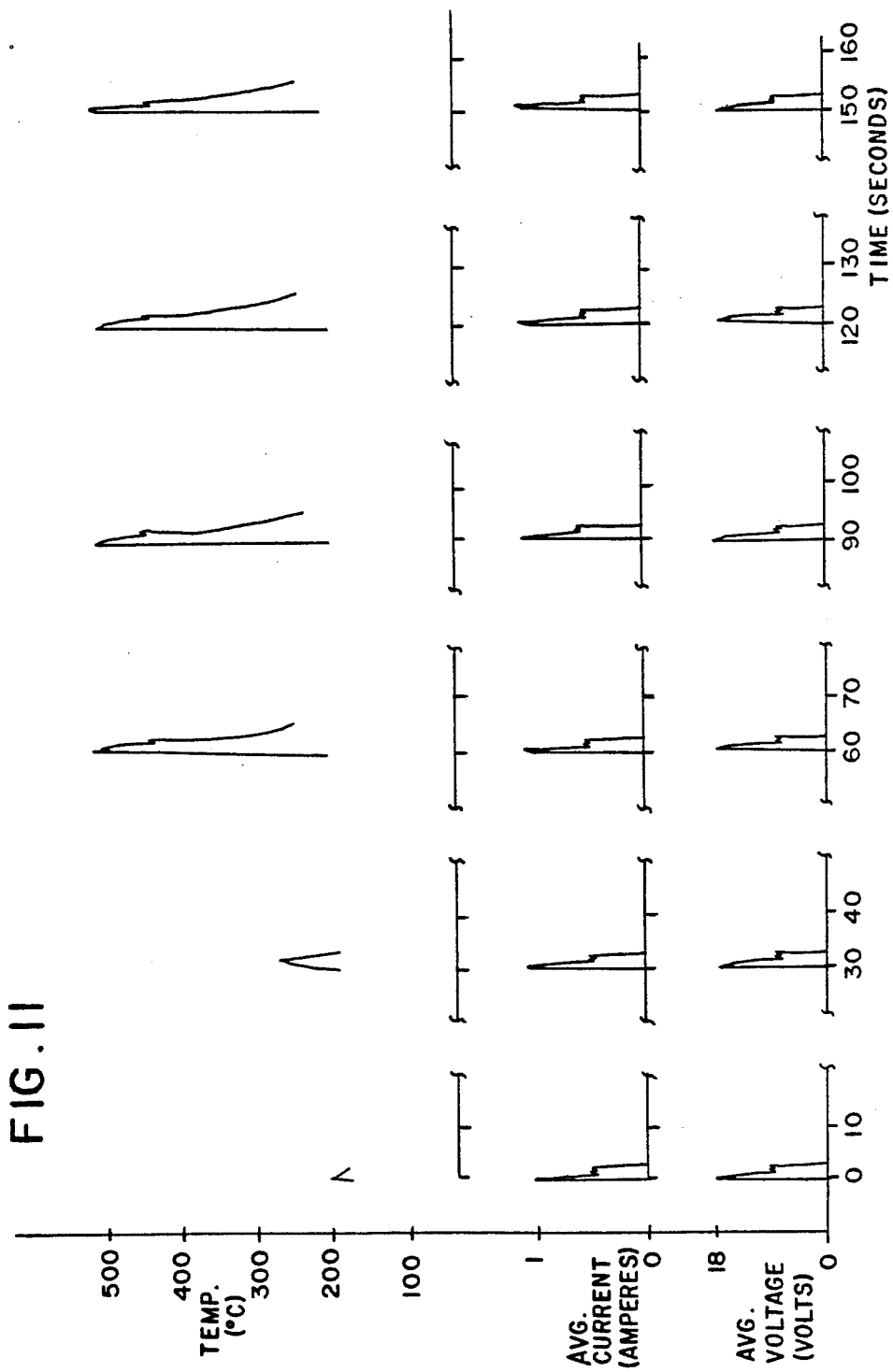
FIG. 11 depicts the temperature, average current voltage profiles experienced by a resistance heating element during heating controlled by the preferred current regulating means.

As shown in FIG. 11, the maximum temperature reached on the first puff was about 200° C., on the second puff about 350° C., and thereafter about 500° C. Moreover, on each puff, the heating element rapidly achieved the maximum temperature and thereafter maintained that temperature during the balance of the puff, after which the element cooled to ambient temperature over about a 5 second period.

EXAMPLE 4

A flavor delivery article substantially as shown in FIG. 3 was prepared as follows:

A. Preparation of the Disposable Portion

Ceramic receptacle 79 was formed from a 7 mm long, 4 mm diameter section of a ceramic cylinder having two longitudinal, 1.5 mm diameter passageways. The electric resistance heating element 18 was formed from a length of carbon filament yarn obtained from American Kynol, Inc., under Catalogue No. CFY-0204-2 sufficient to provide a measured resistance of 18 ohms when incorporated into the disposable portion. This element was impregnated with 38 mg of a liquid aerosol forming substance comprising 20 $\mu$l of a mixture of glycerin, propylene glycol and triethylene glycol and 5 $\mu$l of an artificial coffee flavor. The ends of the heating element were inserted through the passageways of the receptacle 79 to form a loop, and the ends of the element were folded back over the receptacle. A strip of polyimide film 36 was positioned within the loop to prevent the heating element from contacting itself.

Over the resistance element loop and the receptacle 79 was friction fit a Kapton tube of 4 mm O.D. and a length of 80 mm. The length of the polyimide tube then was enveloped to a diameter of about 8 mm with insulative glass fibers 68 obtained from Owens Corning, Toledo, Ohio, as Glass No. 6437. The glass fibers 68 were enveloped by a non-porous cigarette paper wrap 24, available as P-850-192-2 paper from Kimberly-Clark Corp. The diameter of the resulting rod was 8 mm.

At the end of the rod remote from the ceramic receptacle was positioned a low efficiency cellulose acetate tow (8 denier per filament, 40,000 total denier) filter element 22 having a length of about 10 mm and a diameter of about 8 mm. The rod and filter element were held together using tipping paper.

About 1 mm behind the insulative receptacle 79 were pierced several openings 54 through the paper wrap 24 and the polyimide tube 66 to provide air inlet openings for aerosol formation. The perforations were of about 0.8 mm diameter, which was sufficient to provide the disposable portion with a draw resistance of about 100 mm $H_2O$ pressure drop as determined using a Model No. FTS-300 pressure drop tester from Filtrona Corp.

B. Assembly of the Controller

The controller included a pressure sensitive switch 28, a current control circuit 30, a battery power supply 34A, 34B and a flexible, electric cord 72 which terminated in a cylindrical plug 74.

The cord 72 was a 50 mm length of insulated copper wire. The plug 74 included a ceramic cylinder, having a length of 10 mm and a diameter of 4 mm with two small passageways extending longitudinally therethrough; and a heat resistant bushing made from Zydar from Dartco Mfg., Inc., Augusta, Ga. The cylindrical plug had a diameter of about 8 mm. Copper pins 76, 77 connected to cord 72 were inserted through the passageways in the ceramic cylinder to extend 10 mm beyond the face of the plug.

The pressure sensitive switch 28 was a Model No. MPL-502-V, range A, differential switch obtained from Micro Pneumatic Logic, Inc. A 12 mm long, 18 gauge steel needle was inserted into the appropriate opening in the switch.

The control circuit employed is schematically illustrated in FIG. 10. It was designed to provide uninterrupted current flow through the heating element for 2 seconds after the commencement of a puff. During the balance of the puff, the control circuit was designed to alternately switch off for 1 second and then on for 2 seconds, until the pressure actuated control switch opened. Timer 112 was a Model C-1555C obtained from NEC Electronics. Connections to timer 112 were made at trigger pin 168, threshold pin 169, output pin 159, discharge pin 166, entrance pin 149 and ground pin 151. Transistor 110 was a Model MJE 2955 from Motorola Semiconductor Products. Capacitor 190 had a capacitance of 22 $\mu$F. The resistances of the resistors 176, 178 and 180 were 20,000 ohm; 120,000 ohm; and 68,000 ohm, respectively. Resistors 161 and 192 each had resistances of 1,000 ohm.

The control circuit was connected to the switch, the cord 72, and the battery terminals, as schematically illustrated in FIG. 10. The battery supply consisted of two 9 volt alkaline transistor batteries connected in series.

C. Use

The pins 76, 77 of plug 74 were inserted into receptacle 79 to contact the heating element 18 and hence electrically connect the disposable portion to the controller by contacting each end of the resistance element 18. The needle 48 was pierced through the outer wrap 24 and the polyimide tube 66 of the disposable portion.

The mouthend of the disposable portion was placed in the mouth of the user, and the article was drawn upon. Visible, flavored aerosol was provided during each puff, and during each puff period, the indicator light illuminated.

EXAMPLE 5

A flavor delivery article substantially as shown in FIG. 4 was prepared as follows:

A. Preparation of the Disposable Portion

Electrically insulative plug 16 was formed from a Delrin cylinder to have a 2 mm long section of 8 mm diameter and a 3 mm long section of 7 mm diameter. The plug was provided with a passageway 46 of sufficient size to receive an 18 gauge needle and two smaller passageways to receive electrical connector pins 38, 39.

The pins 38, 39 were gold plated copper pins which extended through the passageways in the plug, beyond the 8 mm O.D. end of the plug, and 3 mm beyond the 7 mm O.D. end. The pins had a flattened bead of silver solder applied at the ends which extended beyond the 7 mm O.D. end.

An insulative collar 49 was formed from a Delrin cylinder having a length of 9 mm and a diameter of 8 mm to a tubular form having a 3 mm segment of 4.5 mm I.D. and a 6 mm segment of 6 mm I.D. A single air inlet 54 was made about 4 mm from the 6 mm I.D. end of the collar.

The electric resistance heating element 18 was formed from a 6 mm diameter circular disc of carbon filament felt obtained from American Kynol as Kynol Activated Carbon Felt ACN-211-10. The resistance element weighed about 8 mg and had a reported resistivity of 20 to 30 ohms-cm. The felt had a liquid, flavored aerosol forming substance applied thereto in a dropwise manner. The aerosol forming substance was 25 μl of a mixture of glycerin, triethylene glycol and propylene glycol, and 20 μl of an artificial coffee flavor.

The resistance element 18 was inserted into the 6 mm I.D. end of the collar 49 to abut against the 4.5 mm I.D. portion of the collar.

The 6 mm I.D. end of the collar 48 then was fit over the narrow end of plug 16 such that the flattened silver solder ends of pins 38 and 39 each contacted the resistance element 18.

A resilient paperboard tube having an 8 mm O.D. and a length of 75 mm was abutted against the end of collar 49 opposite plug 16, and the two tubes were held in place using adhesive tape 52.

B. Use

The plug 16 was placed against receptacle 88 of the controller described in Example 1 to electrically connect the disposable portion to the controller and insert the needle 48 into the disposable portion. The mouthend of the disposable portion was placed in the mouth of the user, and the article was drawn upon. Visible aerosol having a coffee flavor was provided on all puffs for 8 puffs.

What is claimed is:

1. A disposable portion of a flavor delivery article containing a flavor substance for use with a source of electrical power comprising:
   (a) an electrical resistance heating element having a surface area greater than 1 $m^2/g$; and
   (b) aerosol forming substance carried by the heating element prior to use.

2. The disposable article of claim 1, wherein the heating element has a surface area greater than 50 $m^2/g$.

3. The disposable article of claim 1, wherein the heating element has a surface area greater than 250 $m^2/g$.

4. The disposable article of claim 1, wherein the heating element has a surface area greater than 1,000 $m^2/g$.

5. The disposable article of claim 1, 2, 3 or 4, wherein the heating element comprises a porous material and the aerosol forming substance comprises a liquid impregnated within the heating element.

6. The disposable article of claim 1, 2, 3 or 4, wherein the heating element is a fibrous material.

7. The disposable article of claim 1, 2, 3 or 4, wherein the heating element comprises a fibrous material and the aerosol forming substance comprises a liquid impregnated within the fibrous material.

8. The disposable article of claim 1, 2, 3 or 4, wherein the heating element comprises carbon fibers.

9. The disposable article of claim 1, 2, 3 or 4, wherein the heating element comprises carbon fibers and the aerosol forming substance comprises a liquid impregnating the carbon fibers.

10. The disposable article of claim 1, wherein the disposable article includes an air passageway at least partially therethrough, and the electrical resistance element comprises an air permeable heating element positioned in the passageway.

11. The disposable article of claim 10, wherein the heating element is positioned substantially perpendicularly to the longitudinal axis of the air passageway.

12. The disposable article of claim 10, wherein the heating element is disposed substantially across the passageway.

13. The disposable article of claim 10, wherein the heating element comprises a pad positioned across the air passageway.

14. The disposable article of claim 10, 11, 12 or 13, wherein the heating element has a surface area greater than 50 $m^2/g$.

15. The disposable article of claim 10, 11, 12 or 13, wherein the heating element has a surface area greater than 1,000 $m^2/g$.

16. The disposable article of claim 10, 11, 12 or 13, wherein the heating element comprises carbon fibers.

17. The disposable article of claim 1, 10, 11, 12 or 13, wherein the heating element is positioned adjacent one end of the article.

18. The disposable article of claim 17, wherein the heating element is adapted for connection to an external source of electrical power.

19. The disposable article of claim 1, 10, 11, 12 or 13, including means for connecting the heating element to an external source of electrical power.

20. The disposable article of claim 19, wherein the means for connecting the heating element to the external source of electrical power includes an air passageway.

21. The disposable article of claim 19, including an air outlet for delivering aerosol to the user, and wherein the air outlet and the means for connecting the heating element to the external source of electrical power are at opposite ends of the disposable article.

22. The disposable article of claim 19, including an air outlet for delivering aerosol to the user and wherein the air outlet and the means for connecting the heating element to the external source of electrical power are at the same end of the disposable article.

23. The disposable article of claim 1, 2, 3, 4 or 10, wherein the aerosol forming substance includes a flavor substance.

24. The disposable article of claim 1, 2, 3, 4 or 10, wherein the aerosol forming substance includes a flavor substance and at least one polyhydric alcohol.

25. The disposable article of claim 1, 2, 3, 4 or 10, wherein the flavor substance is carried by the heating element prior to use.

26. The disposable article of claim 1, 2, 3, 4 or 10, wherein the article includes a mouth end, and the flavor substance is located between the heating element and the mouth end of the article.

27. The disposable article of claim 10, 11, 12 or 13, wherein the aerosol forming substance is a liquid impregnated within the electrical resistance element.

28. The disposable article of claim 1, 10 or 13, in the form of a cartridge.

29. A disposable portion of a flavor delivery article containing a flavor substance for use with a source of electrical power comprising:
    (a) an air passageway at least partially through the disposable portion;
    (b) an air permeable electrical heating element located in the air passageway; and
    (c) an aerosol forming substance.

30. The disposable article of claim 29, wherein the heating element is positioned substantially perpendicularly to the longitudinal axis of the air passageway.

31. The disposable article of claim 29, wherein the heating element substantially fills the cross sectional area of the air passageway.

32. The disposable article of claim 29, wherein the heating element comprises a pad positioned across the air passageway.

33. The disposable article of claim 29, 30, 31 or 32, wherein the aerosol forming substance is carried by the heating element prior to use.

34. The disposable article of claim 29, 30, 31 or 32, wherein the heating element comprises a fibrous mass.

35. The disposable article of claim 34, wherein the aerosol forming substance is a liquid carried by the fibrous mass.

36. The disposable article of claim 29, 30, 31 or 32, wherein the heating element comprises carbon fibers.

37. The disposable article of claim 36, wherein the aerosol forming substance is a liquid carried by the carbon fibers.

38. The disposable article of claim 29, 30, 31 or 32, wherein the heating element is adjacent one end of the article.

39. The disposable article of claim 38, wherein the heating element is adapted for connection to an external source of electrical power.

40. The disposable article of claim 38, including an air outlet for delivering aerosol to the user and wherein the heating element is adjacent the end remote from the air outlet.

41. The disposable article of claim 29, 30, 31 or 32, including an air outlet for delivering aerosol to the user and wherein the heating element is adjacent the air outlet.

42. The disposable article of claim 29, 30, 31 or 32, wherein the aerosol forming substance includes a flavor substance.

43. The disposable article of claim 29, 30, 31 or 32, wherein the flavor substance is carried by the heating element prior to use.

44. The disposable article of claim 29, 30, 31 or 32, wherein the flavor substance is located between the heating element and the mouth end of the article.

45. The disposable article of claim 1, 10, 29 or 32, wherein the article includes sufficient aerosol forming and flavor substances to deliver at least 0.5 mg of wet total particulate matter on each puff, for at least 6 puffs, when the article is puffed under conditions of 2 second, 35 ml puffs, taken every 60 seconds.

46. The disposable article of claim 1, 10, 29 or 32, wherein the article includes sufficient aerosol forming and flavor substances to deliver at least 0.8 mg of wet total particulate matter on each puff, for at least 6 puffs, when the article is puffed under conditions of 2 second, 35 ml puffs, taken every 60 seconds.

47. The disposable article of claim 1, 10, 29 or 32, wherein the aerosol forming and flavor substances comprise a liquid, and wherein the article includes sufficient aerosol forming and flavor substances to deliver at least 0.5 mg of wet total particulate matter on each puff, for at least 6 puffs, when the article is puffed under conditions of 2 second, 35 ml puffs, taken every 60 seconds.

48. A flavor delivery article containing a flavor substance or use with a source of electrical power comprising:
    (a) an electrical resistance heating element having a surface area greater than 1 $m^2/g$;
    (b) aerosol forming substance carried by the heating element prior to use; and
    (c) puff actuated control means for permitting current flow through the heating element during draw by the user.

49. The flavor delivery article of claim 48, further including means for regulating current flow through the heating element during draw.

50. The flavor delivery of claim 48 or 49, further comprising a source of electrical power.

51. The flavor delivery article of claim 48 or 49, wherein the heating element comprises a porous material and the aerosol forming substance comprises a liquid impregnated within the heating element.

52. The flavor delivery article of claim 48 or 49, wherein the heating element is a fibrous material.

53. The flavor delivery article of claim 48 or 49, wherein the heating element comprises a fibrous material and the aerosol forming substance comprises a liquid impregnated within the heating element.

54. The flavor delivery article of claim 48 or 49, wherein the heating element comprises carbon fibers.

55. The flavor delivery article of claim 48 or 49, wherein the heating element comprises carbon fibers and the aerosol forming substance comprises a liquid impregnating the carbon fibers.

56. The flavor delivery article of claim 48 or 49, wherein the heating element has a surface area greater than 50 $m^2/g$.

57. The flavor delivery article of claim 48 or 49, wherein the heating element has a surface area greater than 1,000 $m^2/g$.

58. The flavor delivery article of claim 48 or 49, wherein the flavor substance is located between the heating element and the mouth end of the article.

59. The flavor delivery article of claim 48 or 49, wherein the flavor substance is carried by the heating element prior to use.

60. The flavor delivery article of claim 48 or 49, wherein the aerosol forming substance includes a flavor substance.

61. The flavor delivery article of claim 48 or 49, wherein the aerosol forming substance includes at least one polyhydric alcohol.

62. The flavor delivery article of claim 49, wherein the means for regulating current flow during draw comprises a timer.

63. The flavor delivery article of claim 62, wherein the means for regulating current flow during draw further comprises a timer responsive switching means for enabling and disabling current flow to the resistance element during draw.

64. The flavor delivery article of claim 49, 62 or 63, wherein the means for regulating current flow during draw includes a capacitor and means for charging and discharging the capacitor at a rate which approximates a rate at which the resistance element heats and cools.

65. The flavor delivery article of claim 49, wherein the means for regulating current flow during draw comprises (i) means for permitting uninterrupted current flow through the resistance element for an initial time period during draw, and (ii) means for subsequently regulating current flow until draw is completed.

66. The flavor delivery article of claim 65, wherein the means for subsequently regulating current flow comprises means for switching the current flow alternately off and on.

67. The flavor delivery article of claim 66, wherein the means for switching the current flow off and on includes means for generating a preset switching cycle.

68. The flavor delivery article of claim 67, wherein the means for generating the preset switching cycle includes a timer.

69. The flavor delivery article of claim 68, wherein the timer generates a periodic digital wave form.

70. The flavor delivery article of claim 49, wherein the means for regulating current flow comprises (i) timer means, activated by the puff control means, for generating a pulse train having a predetermined duty cycle, and (ii) timer responsive switching means for enabling and disabling current flow to the heating element in response to the pulse train from the timer means.

71. The flavor delivery article of claim 49, wherein the means for regulating current flow during draw includes means for controlling the average current flow through the heating element during a portion of the draw.

72. The flavor delivery article of claim 49, wherein the means for regulating current flow during draw includes (i) means for enabling uninterrupted passage of current through the heating element for a predetermined initial time period, and (ii) means for controlling the average current which passes through the heating element upon passage of the predetermined initial time.

73. The flavor delivery article of claim 72, wherein the average current control means comprises (i) timer means for generating a pulse train having a predetermined duty cycle, and (ii) timer responsive switching means for enabling and disabling the current through the electrical heating element in response to the pulse train from the timer means, and wherein the enabling means for the initial time period comprises means for disabling the timer means during the initial time period and enabling the timer means upon passage of the initial time period.

74. The flavor delivery article of claim 73, wherein the enabling means for the initial time period further comprises (i) comparator means for comparing a first voltage at a first input to a threshold voltage at a threshold input and generating an output signal when the first voltage is equal to the threshold voltage, the output signal enabling the timer means; (ii) means for generating the threshold voltage at the threshold input; and (iii) means for generating the threshold voltage at the first input upon passage of the initial time period.

75. The flavor delivery article of claim 49, further comprising means for limiting the temperature of the heating element when a puff occurs before the heating element has cooled after a prior puff.

76. The flavor delivery article of claim 49, wherein the puff actuated control means comprises means for sensing changes in air pressure within the article.

77. A flavor delivery article containing a flavor substance for use with a source of electrical power comprising:
(a) an electrical resistance heating element;
(b) aerosol forming substance;
(c) switch means for actuating and deactuating current flow through the heating element; and
(d) time based means for (i) permitting unrestricted current flow through the heating element for an initial predetermined time period upon current actuation, and (ii) for subsequently regulating current flow until current deactuation.

78. The flavor delivery article of claim 77, wherein the aerosol forming substance is carried by the heating element prior to use.

79. The flavor delivery article of claim 78, wherein the heating element has a surface area greater than 1 $m^2/g$.

80. The flavor delivery article of claim 77, 78 or 79, further comprising a source of electrical power.

81. The flavor delivery article of claim 77, 78 or 79, wherein the heating element comprises a porous material and the aerosol forming substance comprises a liquid impregnated within the heating element.

82. The flavor delivery article of claim 77, 78 or 79, wherein the heating element is a fibrous material.

83. The flavor delivery article of claim 77, 78 or 79, wherein the heating element comprises a fibrous material and the aerosol forming substance comprises a liquid impregnated within the heating element.

84. The flavor delivery article of claim 77, 78 or 9, wherein the heating element comprises carbon fibers.

85. The flavor delivery article of claim 77, 78 or 79, wherein the heating element comprises carbon fibers and the aerosol forming substance comprises a liquid impregnating the carbon fibers.

86. The flavor delivery article of claim 77, 78 or 9, wherein the heating element has a surface area greater than 50 $m^2/g$.

87. The flavor delivery article of claim 77, 78 or 9, wherein the heating element has a surface area greater than 1,000 $m^2/g$.

88. The flavor delivery article of claim 77, 78 or 9, wherein the flavor substance is carried by the heating element prior to use.

89. The flavor delivery article of claim 77, 78 or 9, wherein the aerosol forming substance includes a flavor substance.

90. The flavor delivery article of claim 77, 78 or 79, wherein the aerosol forming substance includes a flavor substance and at least one polyhydric alcohol.

91. The flavor delivery article of claim 77, 78 or 79, wherein the heating element carries sufficient aerosol forming and flavor substances to deliver at least 0.5 mg of wet total particulate matter on each puff, for at least 6 puffs, when puffed under conditions of 2 second, 35 ml puffs, taken every 60 seconds.

92. The flavor delivery article of claim 77, 78 or 79, wherein the means for subsequently regulating current flow until current deactivation includes means for controlling the average current flow through the heating element.

93. The flavor delivery article of claim 77, 78 or 79, wherein the means for permitting current flow for the initial time period and for subsequently regulating current flow until current deactivation includes means for controlling the temperature range to which the heating element is heated during draw.

94. The flavor delivery article of claim 77, 78 or 79, wherein the means for subsequently regulating current flow until current deactivation comprises a timer.

95. The flavor delivery article of claim 77, 78 or 79, wherein the means for subsequently regulating current flow until current deactivation further comprises a timer responsive switching means for enabling and disabling current flow to the heating element.

96. The flavor delivery article of claim 77, 78 or 79, wherein the means for permitting current flow for the initial time period comprises a comparator means.

97. The flavor delivery claim of claim 77, 78 or 79, wherein the means for permitting current flow for the initial time period includes a capacitor and means for charging and discharging the capacitor at a rate which approximates a rate at which the heating element heats and cools.

98. The flavor delivery article of claim 77, 78 or 79, wherein the means for subsequently regulating current flow comprises means for switching the current flow alternately off and on.

99. The flavor delivery article of claim 77, wherein the means for subsequently regulating current flow comprises a timer means for generating a periodic digital wave form having a preset duty cycle.

100. The flavor delivery article of claim 77, wherein the means for subsequently regulating current flow until current deactivation comprises (i) timer means for generating a pulse train having a predetermined duty cycle, and (ii) time responsive switching means for enabling and disabling the current through the electrical heating element in response to the pulse train from the timer means, and wherein the means for permitting current flow for the initial time period comprises means for disabling the timer means during the initial time period and enabling the timer means upon passage of the initial time period.

101. The flavor delivery article of claim 100, wherein the means for permitting current flow for the initial time period further comprises (i) comparator means for comparing a first voltage at a first input to a threshold voltage at a threshold input and generating an output signal when the first voltage is equal to the threshold voltage, the output signal enabling the timer means; (ii) means for generating the threshold voltage at the threshold input; and (iii) means for generating the threshold voltage at the first input upon passage of the initial time period.

102. The flavor delivery article of claim 100 or 101, wherein the means for permitting current flow for the initial time period includes a capacitor and means for charging and discharging the capacitor at a rate which approximates the rate at which the heating element heats and cools.

103. The flavor delivery article of claim 77, wherein the means for permitting current flow for the initial time period and for subsequently regulating current flow comprises (i) timer means, activated by the current actuation and deactuation means, for generating a pulse train having a predetermined duty cycle, and (ii) timer responsive switching means for enabling and disabling current flow to the heating element in response to the pulse train from the timer means.

104. A flavor delivery article containing a flavor substance for use with a source of electrical power comprising:
 (a) an air passageway at least partially through the article;
 (b) an air permeable electrical resistance heating element located in the air passageway;
 (c) an aerosol forming substance;
 (d) puff actuated control means for permitting current flow through the heating element during draw by the user; and
 (e) a mouth end.

105. The flavor delivery article of claim 104, wherein the aerosol forming substance is carried by the heating element.

106. The flavor delivery article of claim 104, further comprising means for regulating current flow through the heating element during draw.

107. The flavor delivery article of claim 106, wherein the aerosol forming substance is carried by the heating element.

108. The flavor delivery article of claim 104, 105, 106 or 107, wherein the aerosol forming substance includes a flavor substance.

109. The flavor delivery article of claim 104, 105, 106 or 107, wherein the flavor substance is carried by the heating element prior to use.

110. The flavor delivery article of claim 104, 105, 106 or 107, wherein the flavor substance is located between the heating element and the mouth end of the article.

111. The flavor delivery article of claim 104, 105, 106 or 107, wherein the heating element is positioned substantially perpendicularly to the longitudinal axis of the air passageway.

112. The flavor delivery article of claim 104, 105, 106 or 107, wherein the heating element substantially fills the cross sectional area of the air passageway.

113. The flavor delivery article of claim 104, 105, 106 or 107, wherein the heating element comprises a pad positioned across the air passageway.

114. The flavor delivery article of claim 104, 105, 106 or 107, wherein the aerosol forming substance is carried by the heating element prior to use.

115. The flavor delivery article of claim 105 or 107, wherein the heating element comprises a fibrous mass.

116. The flavor delivery article of claim 105 or 107, wherein the heating element comprises a fibrous mass and the aerosol forming substance is a liquid carried by the fibrous mass.

117. The flavor delivery article of claim 105 or 107, wherein the heating element comprises carbon fibers.

118. The flavor delivery article of claim 105 or 107, wherein the heating element comprises carbon fibers and the aerosol forming substance is a liquid carried by the carbon fibers.

119. The flavor delivery article of claim 104, 105, 106 or 107, wherein the heating element is adjacent one end of the article.

120. The flavor delivery article of claim 106, wherein the means for regulating current flow during draw comprises a timer.

121. The flavor delivery article of claim 107, wherein the means for regulating current flow during draw comprises a timer.

122. The flavor delivery article of claim 120, wherein the means for regulating current flow during draw further comprises a timer responsive switching means for enabling and disabling current flow to the heating element during draw.

123. The flavor delivery article of claim 121, wherein the means for regulating current flow during draw further comprises a timer responsive switching means for enabling and disabling current flow to the heating element during draw.

124. The flavor delivery article of claim 106, 107, 120 or 121, wherein the means for regulating current flow during draw includes a capacitor and means for charging and discharging the capacitor at a rate which approximates a rate at which the heating element heats and cools.

125. The flavor delivery article of claim 106, wherein the means for regulating current flow during draw comprises (i) means for permitting uninterrupted current flow through the heating element for an initial time period during draw, and (ii) means for subsequently regulating current flow until draw is completed.

126. The flavor delivery article of claim 125, wherein the means for subsequently regulating current flow comprises means for switching the current flow alternately off and on.

127. The flavor delivery article of claim 126, wherein the means for switching the current flow off and on includes means for generating a preset switching cycle.

128. The flavor delivery article of claim 127, wherein the means for generating the preset switching cycle includes a timer.

129. The flavor delivery article of claim 128, wherein the timer generates a periodic digital wave form.

130. The flavor delivery article of claim 106, wherein the means for regulating current flow comprises (i) timer means, activated by the puff control means, for generating a pulse train having a predetermined duty cycle, and (ii) timer responsive switching means for enabling and disabling current flow to the heating element in response to the pulse train from the timer means.

131. The flavor delivery article of claim 106, wherein the means for regulating current flow during draw includes means for controlling the average current flow through the heating element during a portion of the draw.

132. The flavor delivery article of claim 106, wherein the means for regulating current flow during draw includes (i) means for enabling unrestricted passage of current through the resistance element for a predetermined initial time period, and (ii) means for controlling the average current which passes through the resistance element upon passage of the predetermined initial time.

133. The flavor delivery article of claim 132, wherein the average current control means comprises (i) timer means for generating a pulse train having a predetermined duty cycle, and (ii) timer responsive switching means for enabling and disabling the current through the electrical resistance element in response to the pulse train from the timer means, and wherein the enabling means for the initial time period comprises means for disabling the timer means during the initial time period and enabling the timer means upon passage of the initial time period.

134. The flavor delivery article of claim 133, wherein the enabling means for the initial time period further comprises (i) comparator means for comparing a first voltage at a first input to a threshold voltage at a threshold input and generating an output signal when the first voltage is equal to the threshold voltage, the output signal enabling the timer means; (ii) means for generating the threshold voltage at the threshold input; and (iii) means for generating the threshold voltage at the first input upon passage of the initial time period.

135. The flavor delivery article of claim 108, further comprising means for limiting the temperature of the heating element when a puff occurs before the heating element has cooled after a prior puff.

136. The flavor delivery article of claim 105, wherein the puff actuated control means comprises means for sensing changes in air pressure within the article.

* * * * *